United States Patent [19]
Katsura et al.

[11] Patent Number: 5,892,094
[45] Date of Patent: Apr. 6, 1999

[54] PROCESS FOR PREPARING 4'-METHYL-2-CYANOBIPHENYL

[75] Inventors: Tadashi Katsura; Hiroshi Shiratani; Kiyoshi Sugi; Nobushige Itaya, all of Osaka, Japan

[73] Assignee: Sumika Fine Chemicals Co., Ltd., Osaka, Japan

[21] Appl. No.: 996,341

[22] Filed: Dec. 22, 1997

[30] Foreign Application Priority Data

Jan. 8, 1997 [JP] Japan .................................. 9-013439

[51] Int. Cl.$^6$ .................................................. C07C 255/00
[52] U.S. Cl. ......................................................... 558/378
[58] Field of Search .............................................. 558/378

[56] References Cited

U.S. PATENT DOCUMENTS 5,288,895  2/1994  Bousset et al. .......................... 558/378

FOREIGN PATENT DOCUMENTS

0709369A1  5/1996  European Pat. Off. .

OTHER PUBLICATIONS

Marques, C.A., Selva, M., Tundo, P., "Hydrodehalogenation of Polyhalogenated Aromatics Under Multiphase Conditions with H2 and Metal Catalyst", Gazz. Chim. Ital., 126(6), 317–327, 1996.

*Primary Examiner*—Johann Richter
*Assistant Examiner*—Joseph Murray
*Attorney, Agent, or Firm*—Birch, Stewart, Kolasch & Birch, LLP

[57] ABSTRACT

Process for preparing 4'-methyl-2-cyanobiphenyl, comprising, catalytically hydrogenating at least one brominated cyanobiphenyl compound selected from 4'-dibromomethyl-2-cyanobiphenyl and 4'-bromomethyl-2-cyanobiphenyl; and process for regenerating 4'-methyl-2-cyanobiphenyl, comprising, catalytically hydrogenating at least one brominated cyanobiphenyl compound selected from 4'-dibromomethyl-2-cyanobiphenyl and 4'-bromomethyl-2-cyanobiphenyl, contained in a filtrate prepared by brominating 4'-methyl-2-cyanobiphenyl in a solvent; crystallizing 4'-bromomethyl-2-cyanobiphenyl from the resulting reaction mixture; and removing the resulting crystals from the reaction mixture by filtration. 4'-Methyl-2-cyanobiphenyl can be used as starting materials for 4'-bromomethyl-2-cyanobiphenyl.

12 Claims, No Drawings

PROCESS FOR PREPARING 4'-METHYL-2-CYANOBIPHENYL

BACKGROUND OF THE INVENTION

1. Field of the Invention

The present invention relates to a process for preparing 4'-methyl-2-cyanobiphenyl. More particularly, the present invention relates to a process for preparing 4'-methyl-2-cyanobiphenyl, which is useful as an intermediate of 4'-bromomethyl-2-cyanobiphenyl used as starting materials of pharmaceuticals such as antihypertensives, and also relates to a process for regenerating 4'-methyl-2-cyanobiphenyl from by-products formed during the preparation of 4'-bromomethyl-2-cyanobiphenyl from 4'-methyl-2-cyanobiphenyl.

2. Discussion of the Related Art

Conventionally, there have been known a process for preparing 4'-bromomethyl-2-cyanobiphenyl, comprising dissolving 4'-methyl-2-cyanobiphenyl in a solvent; brominating the 4'-methyl-2-cyanobiphenyl; crystallizing the resulting 4'-bromomethyl-2-cyanobiphenyl; and collecting the resulting crystals by filtration as disclosed in U.S. Pat. No. 5,621,134, corresponding to Japanese Patent Laid-Open No. Hei 8-127562.

In the above process, there are some advantageous merits in being able to industrially and advantageously prepare 4'-bromomethyl-2-cyanobiphenyl from inexpensive starting materials in a high yield.

However, in the above process, after crystallizing 4'-bromomethyl-2-cyanobiphenyl from the reaction mixture and collecting the obtained crystals by filtration, the resulting filtrate contains 4'-dibromomethyl-2-cyanobiphenyl as a by-product as well as 4'-bromomethyl-2-cyanobiphenyl which remains in a mother liquor.

Therefore, the development of a process of efficiently reusing the by-product, 4'-dibromomethyl-2-cyanobiphenyl and the remaining desired compound, 4'-bromomethyl-2-cyanobiphenyl contained in the filtrate has been highly desired.

In view of the problems in the prior art mentioned above, an object of the present invention is to provide a process of efficiently reusing the by-product, 4'-dibromomethyl-2-cyanobiphenyl and the remaining desired compound, 4'-bromomethyl-2-cyanobiphenyl contained in the filtrate.

These and other objects of the present invention will be apparent from the following description.

SUMMARY OF THE INVENTION

Specifically, the present invention pertains to the following:

(1) A process for preparing 4'-methyl-2-cyanobiphenyl, comprising the step of:
catalytically hydrogenating at least one brominated cyanobiphenyl compound selected from the group consisting of 4'-dibromomethyl-2-cyanobiphenyl and 4'-bromomethyl-2-cyanobiphenyl; and (2) A process for regenerating 4'-methyl-2-cyanobiphenyl, comprising the step of:
catalytically hydrogenating at least one brominated cyanobiphenyl compound selected from the group consisting of 4'-dibromomethyl-2-cyanobiphenyl and 4'-bromomethyl-2-cyanobiphenyl, contained in a filtrate prepared by brominating 4'-methyl-2-cyanobiphenyl in a solvent;
crystallizing 4'-bromomethyl-2-cyanobiphenyl from the resulting reaction mixture; and
removing the resulting crystals from the reaction mixture by filtration.

DETAILED DESCRIPTION OF THE INVENTION

4'-Methyl-2-cyanobiphenyl is used, for instance, as a starting material for 4'-bromomethyl-2-cyanobiphenyl. 4'-Bromomethyl-2-cyanobiphenyl can be prepared from 4'-methyl-2-cyanobiphenyl, for instance, by a process disclosed in U.S. Pat. No. 5,621,134, corresponding to Japanese Patent Laid-Open No. Hei 8-127562.

Concretely, 4'-bromomethyl-2-cyanobiphenyl can be prepared by brominating 4'-methyl-2-cyanobiphenyl in a halogenated hydrocarbon solvent or an alkane solvent having 5 to 7 carbon atoms in the presence of a radical initiator. The resulting 4'-bromomethyl-2-cyanobiphenyl obtained by the above process can be collected, for instance, by distilling off the solvent, recrystallizing from the other suitable solvent, and isolating and purifying the resulting crystals from the solvent.

However, after the obtained crystals are collected, the filtrate contains the by-product, 4'-dibromomethyl-2-cyanobiphenyl as well as the remaining desired compound, 4'-bromomethyl-2-cyanobiphenyl.

According to the process of the present invention, the by-product, 4'-dibromomethyl-2-cyanobiphenyl as well as the remaining desired compound, 4'-bromomethyl-2-cyanobiphenyl contained in the filtrate can be easily converted to a starting material, 4'-methyl-2-cyanobiphenyl for the preparation of 4'-bromomethyl-2-cyanobiphenyl.

In other words, when at least one brominated cyanobiphenyl compound selected from the group consisting of 4'-dibromomethyl-2-cyanobiphenyl and 4'-bromomethyl-2-cyanobiphenyl is catalytically hydrogenated according to the process of the present invention, it has been marvelously found out that 4'-methyl-2-cyanobiphenyl, which can be used as a starting material for preparing 4'-bromomethyl-2-cyanobiphenyl, can be efficiently prepared. Moreover, it has also been found out that the thus regenerated 4'-methyl-2-cyanobiphenyl can be reused in the preparation of 4'-bromomethyl-2-cyanobiphenyl.

Therefore, the process of the present invention enjoys advantageous merits in remarkably increasing the industrial productivity of 4'-bromomethyl-2-cyanobiphenyl obtained by brominating 4'-methyl-2-cyanobiphenyl.

In the present invention, there are the following embodiments for catalytically hydrogenating at least one brominated cyanobiphenyl compound selected from the group consisting of 4'-dibromomethyl-2-cyanobiphenyl and 4'-bromomethyl-2-cyanobiphenyl:

(1) A process comprising mixing at least one brominated cyanobiphenyl compound selected from the group consisting of 4'-dibromomethyl-2-cyanobiphenyl and 4'-bromomethyl-2-cyanobiphenyl, at least one member selected from the group consisting of an inorganic base and a tertiary amine, a catalyst, and a solvent, and catalytically hydrogenating the resulting mixture while introducing hydrogen gas in the mixture (hereinafter referred to as "Process I"); and (2) A process comprising mixing at least one member selected from the group consisting of an inorganic base and a tertiary amine, a catalyst, and a solvent, and adding dropwise a solution of at least one brominated cyanobiphenyl compound selected from 4'-dibromomethyl-2-cyanobiphenyl and 4'-bromomethyl-2-cyanobiphenyl to the resulting mixture while introducing hydrogen gas in the mixture (hereinafter referred to as "Process II").

In Process I mentioned above, the starting material of at least one brominated cyanobiphenyl compound selected from the group consisting of 4'-dibromomethyl-2-cyanobiphenyl and 4'-bromomethyl-2-cyanobiphenyl (hereinafter simply referred to as "brominated cyanobiphenyl compound"), for instance, include the filtrate obtained through the process for preparing 4'-bromomethyl-2-cyanobiphenyl from 4'-methyl-2-cyanobiphenyl according to a process disclosed in U.S. Pat. No. 5,621,134, corresponding to Japanese Patent Laid-Open No. Hei 8-127562, i.e. crystallizing the resulting 4'-bromomethyl-2-cyanobiphenyl, and filtrating the crystals. The obtained filtrate contains the by-product, 4'-dibromomethyl-2-cyanobiphenyl as well as the remaining desired compound, 4'-bromomethyl-2-cyanobiphenyl. The process of the present invention enjoys the advantageous merits of being able to efficiently obtain 4'-methyl-2-cyanobiphenyl from these compounds, and further enjoys merits of being able to reuse the thus regenerated 4'-methyl-2-cyanobiphenyl in the preparation of 4'-bromomethyl-2-cyanobiphenyl.

Concrete examples of the inorganic bases usable in Process I include sodium hydroxide, sodium carbonate, potassium carbonate, calcium carbonate, sodium acetate, and the like. The amount of the inorganic base is not particularly limited. From the aspects of acceleration of reaction and improvements in yield, it is desired that the amount of the inorganic base is at least one mole, preferably from one to two moles, per one mole of bromine atoms in the brominated cyanobiphenyl compound.

Concrete examples of the tertiary amines usable in Process I include triethylamine, pyridine, and the like. The amount of the tertiary amine is not particularly limited. From the aspects of acceleration of reaction and improvements in yield, it is desired that the amount of the tertiary amine is at least one mole, preferably from one to two moles, per one mole of bromine atoms in the brominated cyanobiphenyl compound.

In the present invention, the above inorganic base and the tertiary amine can be used in combination. In a case where both the inorganic base and the tertiary amine are used, the total amount of the inorganic base and the tertiary amine is not particularly limited. From the aspects of acceleration of reaction and increase in yield, it is desired that the total amount is at least one mole, preferably from one to two moles per one mole of bromine atoms in the brominated cyanobiphenyl compound.

Examples of the catalysts usable in Process I include nickel catalysts such as Raney nickel, palladium catalysts such as Pd—C, platinum catalysts such as Pt—C, and the like. The amount of the catalyst is not particularly limited. From the aspects of acceleration of reaction and increase in yield, it is desired that the amount of the catalyst is at least 1% by weight, preferably from 2 to 20% by weight to the total amount of the brominated cyanobiphenyl compound.

The solvents usable in Process I can be any kind as long as they are not reactive with the brominated cyanobiphenyl compound. The solvents include, for instance, alcohols, ethers, esters, aromatic hydrocarbons, mixtures thereof, and the like. Incidentally, the solvents may include water, as occasion demands.

Examples of the alcohols include methanol, ethanol, isopropanol, butanol, and the like. Examples of the ethers include tetrahydrofuran, diisopropyl ether, t-butyl methyl ether, and the like. Examples of the esters include ethyl acetate, methyl acetate, and the like. Examples of the aromatic hydrocarbons include toluene, benzene, xylene, ethylbenzene, and the like.

The amount of the solvent is not particularly limited. It is desired that the amount of the solvent is at least 100 parts by weight, preferably from 200 to 1000 parts by weight, based on 100 parts by weight of the brominated cyanobiphenyl compound.

The temperature during the catalytic hydrogenation is not particularly limited. It is desired that the temperature during the catalytic hydrogenation is not lower than 0° C., preferably from 10° to 50° C. The reaction time cannot be absolutely determined because the reaction time can differ depending upon the reaction temperature, and the like. The reaction time is usually from 2 to 10 hours or so.

The pressure of hydrogen gas blown in the mixture during the catalytic hydrogenation is not particularly limited. The pressure is preferably from 1 to 5 atm or so. Also, it is desired that the amount of the hydrogen gas blown therein is at least one mole, per one mole of bromine atoms of the brominated cyanobiphenyl compound.

Process II will be then explained in detail.

The brominated cyanobiphenyl compounds, the inorganic bases, the tertiary amines, the catalysts, and the solvents which are usable in Process II can be similar to those usable in Process I.

In Process II, the solvent which can be used for dissolving the brominated cyanobiphenyl compound can be similar to those listed as the solvents usable in Process I. The amount of the solvent is not particularly limited. It is desired that the amount of the solvent is not less than 100 parts by weight, preferably from 200 to 1,000 parts by weight, based on 100 parts by weight of the brominated cyanobiphenyl compound.

In Process II, the conditions such as temperature, period of time, and pressure and amount of hydrogen gas during the catalytic hydrogenation can be similar to those described in Process I.

The resulting 4'-methyl-2-cyanobiphenyl prepared by Process I or Process II can be suitably used as a starting compound for preparing 4'-bromomethyl-2-cyanobiphenyl, which is useful as an intermediate for starting materials of pharmaceuticals such as oral antihypertensives.

EXAMPLES

The present invention will be more specifically described by the following examples, without intending to restrict the scope or spirit of the present invention thereto.

Preparation Example 1

Preparation of Mixture of 4'-Dibromomethyl-2-cyanobiphenyl and 4'-Bromomethyl-2-cyanobiphenyl A 500-ml four-necked flask was charged with 55.0 g (0.202 mol) of 4'-bromomethyl-2-cyanobiphenyl, 250 g of dichloromethane, and 0.66 g (4 mmol) of 2,2'-azobisisobutyronitrile. Thereafter, 16.4 g (0.1026 mol) of bromine was added dropwise to the above mixture under reflux with heating to about 40° C. over a period of five hours, and the temperature of the mixture was then kept at about 40° C. for one hour. After terminating the reaction, dichloromethane was distilled off, to give 62.3 g of a mixture of 4'-dibromomethyl-2-cyanobiphenyl and 4'-bromomethyl-2-cyanobiphenyl.

The resulting mixture was analyzed by liquid chromatography (hereinafter simply referred to as "LC"). As a result, it was found that the mixture contained 43.9% of 4'-dibromomethyl-2-cyanobiphenyl and 56.1% of 4'-bromomethyl-2-cyanobiphenyl.

Example 1

In a one-liter four-necked flask, 500 ml of methanol, 6.0 g of 5% Pd—C, and 14.4 g of sodium hydroxide were mixed together and stirred to prepare a suspension of Pd—C. The atmosphere in the flask was then replaced with nitrogen gas, and thereafter the atmosphere was further replaced with hydrogen gas.

The temperature inside the flask was adjusted to 20° to 25° C. Thereafter, while hydrogen gas was blown in the flask and the mixture was vigorously stirred, a solution previously prepared by dissolving 62.3 g of the mixture of 4'-dibromomethyl-2-cyanobiphenyl and 4'-bromomethyl-2-cyanobiphenyl obtained in Preparation Example 1 in 100 ml of tetrahydrofuran was added dropwise from a dropping funnel to the above suspension over a period of three hours.

After the dropwise addition of the solution prepared by dissolving the mixture of 4'-dibromomethyl-2-cyanobiphenyl and 4'-bromomethyl-2-cyanobiphenyl in tetrahydrofuran was terminated, the mixture was allowed to react up to a point where the above suspension no longer absorbs hydrogen gas.

After the reaction was terminated, Pd—C and sodium hydroxide were filtered off, and the reaction mixture was then concentrated to distill off methanol. The resulting crude 4'-methyl-2-cyanobiphenyl was purified by distillation, to give 37.3 g of 4'-methyl-2-cyanobiphenyl having an LC purity of 98.0%.

Example 2

A one-liter four-necked flask was charged with 50 g (0.2588 mol) of 4'-methyl-2-cyanobiphenyl, 375 g of monochlorobenzene, and 0.85 g (5.18 mmol) of 2,2'-azobisisobutyronitrile, and the temperature inside the flask was controlled to 60° to 65° C. Thereafter, 41.5 g (0.2597 mol) of bromine was added dropwise to the above reaction mixture at 60° to 65° C. over a period of five hours, and the temperature of the mixture was then kept at 60° to 65° C. for one hour. At this stage, a sample was taken out from the reaction mixture to conduct LC analysis. It was found that the mixture contained 3.0% of 4'-methyl-2-cyanobiphenyl, 89.5% of 4'-bromomethyl-2-cyanobiphenyl, and 6.7% of 4'-dibromomethyl-2-cyanobiphenyl. Therefore, the selectivity of 4'-bromomethyl-2-cyanobiphenyl was 93.0%.

Thereafter, the reaction mixture was concentrated to distill off 150 g of the solvent, monochlorobenzene. Subsequently, 225 g of n-hexane was added thereto and the reaction was allowed to be crystallized therefrom, to give 58.8 g of 4'-bromomethyl-2-cyanobiphenyl having an LC purity of 98.7%. The yield was 83.5% based on 4'-methyl-2-cyanobiphenyl.

n-Hexane was distilled off from the remaining mother liquor obtained after the filtration of 4'-bromomethyl-2-cyanobiphenyl, to give a 12.0 g mixture of 4'-dibromomethyl-2-cyanobiphenyl and 4'-bromomethyl-2-cyanobiphenyl. The resulting mixture was analyzed by LC. As a result, it was found that the mixture contained 19.1% of 4'-methyl-2-cyanobiphenyl, 38.2% of 4'-bromomethyl-2-cyanobiphenyl, and 42.7% of 4'-dibromomethyl-2-cyanobiphenyl.

In a 300-ml four-necked flask, 100 ml of methanol, 1.2 g of Raney nickel, and 6.4 g of sodium carbonate were mixed together and stirred to prepare a suspension of Raney nickel. Subsequently, the atmosphere in the flask was replaced with nitrogen gas, and the atmosphere was then further replaced with hydrogen gas.

The temperature inside the flask was adjusted to 20° to 25° C. Thereafter, while hydrogen gas was blown in the flask and the mixture was vigorously stirred, a solution previously prepared by dissolving 12.0 g of the mixture of 4'-dibromomethyl-2-cyanobiphenyl and 4'-bromomethyl-2-cyanobiphenyl prepared above in 30 g of toluene was added dropwise from a dropping funnel to the above suspension over a period of three hours.

After the dropwise addition of the solution prepared by dissolving the mixture of 4'-dibromomethyl-2-cyanobiphenyl and 4'-bromomethyl-2-cyanobiphenyl in toluene was terminated, the mixture was allowed to react up to a point where the above suspension no longer absorbs hydrogen gas. After the reaction was terminated, Raney catalyst and sodium carbonate were filtered off, and the reaction mixture was then concentrated to distill off methanol and toluene. The resulting crude 4'-methyl-2-cyanobiphenyl was purified by distillation, to give 7.4 g of 4'-methyl-2-cyanobiphenyl having an LC purity of 98.2%.

Example 3

A two-liter four-necked flask was charged with 150 g (0.7764 mol) of 4'-methyl-2-cyanobiphenyl, 900 g of monochlorobenzene, and 2.55 g (15.5 mmol) of 2,2'-azobisisobutyronitrile, and the temperature inside the flask was controlled to 60° to 65° C. Thereafter, 124.5 g (0.7791 mol) of bromine was added dropwise to the above reaction mixture at 60° to 65° C. over a period of five hours, and the temperature of the mixture was then kept at 60° to 65° C. for one hour. At this stage, a sample was taken out from the reaction mixture to conduct LC analysis. It was found that the mixture contained 3.1% of 4'-methyl-2-cyanobiphenyl, 89.6% of 4'-bromomethyl-2-cyanobiphenyl, and 6.6% of 4'-dibromomethyl-2-cyanobiphenyl. Therefore, the selectivity of 4'-bromomethyl-2-cyanobiphenyl was 93.1%.

Thereafter, the reaction mixture was concentrated to distill off 225 g of the solvent, monochlorobenzene. Subsequently, 675 g of n-hexane was added thereto, and the reaction was allowed to be crystallized therefrom, to give 180.5 g of 4'-bromomethyl-2-cyanobiphenyl having an LC purity of 98.5%. The yield was 85.4% based on 4'-methyl-2-cyanobiphenyl.

n-Hexane was distilled off from the remaining mother liquor obtained after the filtration of 4'-bromomethyl-2-cyanobiphenyl, to give a 35.6 g mixture of 4'-dibromomethyl-2-cyanobiphenyl and 4'-bromomethyl-2-cyanobiphenyl. The resulting mixture was analyzed by LC. As a result, it was found that the mixture contained 19.5% of 4'-methyl-2-cyanobiphenyl, 37.4% of 4'-bromomethyl-2-cyanobiphenyl, and 42.6% of 4'-dibromomethyl-2-cyanobiphenyl.

In a one-liter four-necked flask, 300 ml of methanol, 3.6 g of 5% Pt—C, and 7.2 g of sodium hydroxide were mixed together, and stirred to prepare a suspension of Pt—C. Subsequently, the atmosphere in the flask was replaced with nitrogen gas, and the atmosphere was then further replaced with hydrogen gas.

The temperature inside the flask was adjusted to 20° to 25° C. Thereafter, while hydrogen gas was blown in the flask and the mixture was vigorously stirred, a solution previously prepared by dissolving 35.6 g of the mixture of 4'-dibromomethyl-2-cyanobiphenyl and 4'-bromomethyl-2-cyanobiphenyl prepared above in 100 g of toluene was added dropwise from a dropping funnel to the above suspension over a period of three hours.

After the dropwise addition of the solution prepared by dissolving the mixture of 4'-dibromomethyl-2-cyanobiphenyl and 4'-bromomethyl-2-cyanobiphenyl in toluene was terminated, the mixture was allowed to react up to a point where the above suspension no longer absorbs hydrogen gas. After the reaction was terminated, Pt—C and sodium hydroxide were filtered off, and the reaction mixture was then concentrated to distill off methanol and toluene. The resulting crude 4'-methyl-2-cyanobiphenyl was purified by distillation, to give 21.7 g of 4'-methyl-2-cyanobiphenyl having an LC purity of 98.1%.

Example 4

A one-liter four-necked flask was charged with 62.3 g of the mixture of 4'-dibromomethyl-2-cyanobiphenyl and 4'-bromomethyl-2-cyanobiphenyl prepared in the same manner as in Preparation Example 1, 6.0 g of 5% Pt—C, 14.4 g of sodium hydroxide, and 500 ml of tetrahydrofuran, and the resulting mixture was stirred to prepare a suspension of Pt—C. Subsequently, the atmosphere in the flask was replaced with nitrogen gas, and the atmosphere was further replaced with hydrogen gas.

The temperature inside the flask was adjusted to 20° to 25° C. Thereafter, while hydrogen gas was blown in the flask and the mixture was vigorously stirred, the mixture was allowed to react up to a point where the above suspension no longer absorbs hydrogen gas. After the reaction was terminated, Pt—C and sodium hydroxide were filtered off, and the reaction mixture was then concentrated to distill off tetrahydrofuran. The resulting crude 4'-methyl-2-cyanobiphenyl was purified by distillation, to give 36.8 g of 4'-methyl-2-cyanobiphenyl having an LC purity of 98.1%.

It can be seen from the results of Examples 1 to 4 that 4'-methyl-2-cyanobiphenyl can be simply, industrially and advantageously prepared from the brominated cyanobiphenyl compounds.

Therefore, according to the process of the present invention, 4'-methyl-2-cyanobiphenyl can be efficiently regenerated from the filtrate containing the by-product, 4'-dibromomethyl-2-cyanobiphenyl and the desired product, 4'-bromomethyl-2-cyanobiphenyl.

Therefore, according to the process for preparing 4'-methyl-2-cyanobiphenyl of the present invention, such advantageous merits can be exhibited in that 4'-methyl-2-cyanobiphenyl can be efficiently, simply, industrially and advantageously prepared from at least one brominated cyanobiphenyl compound selected from the group consisting of 4'-dibromomethyl-2-cyanobiphenyl and 4'-bromomethyl-2-cyanobiphenyl.

Also, according to the process for regenerating 4'-methyl-2-cyanobiphenyl of the present invention, there can be exhibited such advantageous merits as that 4'-methyl-2-cyanobiphenyl can be efficiently regenerated from a filtrate containing the by-product, 4'-dibromomethyl-2-cyanobiphenyl and the remaining desired compound, 4'-bromomethyl-2-cyanobiphenyl.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A process for preparing 4'-methyl-2-cyanobiphenyl, comprising the steps of:
    (A) mixing at least one member selected from the group consisting of an inorganic base and a tertiary amine, a catalyst, and a solvent to provide a mixture; and
    (B) adding dropwise a solution of at least one brominated cyanobiphenyl compound selected from the group consisting of 4'dibromomethyl-2-cyanobiphenyl and 4'-bromomethyl-2-cyanobiphenyl to the resulting mixture while introducing hydrogen gas into the resulting mixture, to catalytically hydrogenate the brominated cyanobiphenyl compound.

2. The process for preparing 4'-methyl-2-cyanobiphenyl according to claim 1, wherein said inorganic base is sodium hydroxide, sodium carbonate, potassium carbonate, calcium carbonate, or sodium acetate.

3. The process for preparing 4'-methyl-2-cyanobiphenyl according to claim 1, wherein said tertiary amine is triethylamine or pyridine.

4. The process for preparing 4'-methyl-2-cyanobiphenyl according to claim 1, wherein said catalyst is Raney nickel catalyst, Pd—C, or Pt—C.

5. The process for preparing 4'-methyl-2-cyanobiphenyl according to claim 1, wherein said solvent is a solvent which is not reactive with the brominated cyanobiphenyl compound.

6. The process for preparing 4'-methyl-2-cyanobiphenyl according to claim 1, wherein the temperature during the catalytic hydrogenation is 10° to 50° C.

7. A process for regenerating 4'-methyl-2-cyanobiphenyl, comprising the steps of:
    (A) brominating 4'-bromomethyl-2-cyanobiphenyl in a solvent to provide a reaction mixture containing 4'-dibromomethyl-2-cyanobiphenyl and 4'-bromomethyl-2-cyanobiphenyl;
    (B) crystallizing 4'-bromomethyl-2-cyanobiphenyl from the resulting reaction mixture;
    (C) removing the resulting crystallized 4'-bromomethyl-2-cyanobiphenyl from the reaction mixture by filtration;
    (D) mixing at least one member selected from the group consisting of an organic base and a tertiary amine, a catalyst, and a solvent to provide a mixture; and
    (E) adding dropwise the filtrate to the resulting mixture while introducing hydrogen gas into the resulting mixture, to catalytically hydrogenate the brominated cyanobiphenyl compound remaining in the filtrate.

8. The process for regenerating 4'-methyl-2-cyanobiphenyl according to claim 7, wherein said inorganic base is sodium hydroxide, sodium carbonate, potassium carbonate, sodium carbonate, or sodium acetate.

9. The process for regenerating 4'-methyl-2-cyanobiphenyl according to claim 7, wherein said tertiary amine is triethylamine or pyridine.

10. The process for regenerating 4'-methyl-2-cyanobiphenyl according to claim 7, wherein said catalyst is Raney nickel catalyst, Pd—C, or Pt—C.

11. The process for regenerating 4'-methyl-2-cyanobiphenyl according to claim 7, wherein said solvent is a solvent which is not reactive with the brominated cyanobiphenyl compound.

12. The process for regenerating 4'-methyl-2-cyanobiphenyl according to claim 7, wherein the temperature during the catalytic hydrogenation is 10° to 50° C.

* * * * *

UNITED STATES PATENT AND TRADEMARK OFFICE
CERTIFICATE OF CORRECTION

PATENT NO. : 5,892,094
DATED : April 6, 1999
INVENTOR(S) : Tadashi KATSURA et al.

It is certified that error appears in the above-identified patent and that said Letters Patent is hereby corrected as shown below:

IN THE CLAIMS

In claim 7, line 3, change "4'-bromomethyl-2-cyanobiphenyl" to

--4'-methyl-2-cyanobiphenyl--

Signed and Sealed this

Second Day of November, 1999

Attest:

Q. TODD DICKINSON

*Attesting Officer*   Acting Commissioner of Patents and Trademarks